(12) United States Patent
Bordier et al.

(10) Patent No.: US 6,652,600 B2
(45) Date of Patent: Nov. 25, 2003

(54) OXIDATION BASES CONTAINING A GUANIDINE CHAIN, PROCESS FOR PREPARING THEM, THEIR USE FOR THE OXIDATION DYEING OF KERATIN FIBERS, DYE COMPOSITIONS AND DYEING PROCESSES

(75) Inventors: Thierry Bordier, Tremblay en France (FR); Michel Philippe, Wissous (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/770,471

(22) Filed: Jan. 29, 2001

(65) Prior Publication Data

US 2001/0034913 A1 Nov. 1, 2001

(30) Foreign Application Priority Data

Jan. 27, 2000 (FR) .......................................... 00 01055

(51) Int. Cl.$^7$ .................................................. A61K 7/13
(52) U.S. Cl. ........................ 8/405; 8/406; 8/407; 8/408; 8/409; 8/410
(58) Field of Search ............................ 8/405, 406, 407, 8/408, 409, 410

(56) References Cited

U.S. PATENT DOCUMENTS

| 2,185,154 A | * | 12/1939 | Lecher et al. ............... 260/140 |
| 4,731,383 A | * | 3/1988 | Erczi et al. .................. 514/634 |
| 6,042,620 A | * | 3/2000 | Braun et al. .................... 8/410 |
| 6,179,881 B1 | * | 1/2001 | Henrion et al. ................. 8/407 |

OTHER PUBLICATIONS

George et al., J. of Med. Chem., 1971, 14(10), 909–913.*

* cited by examiner

*Primary Examiner*—Mark Kopec
*Assistant Examiner*—Eisa Elhilo
(74) *Attorney, Agent, or Firm*—Finnegan, Henderson, Farabow, Garrett & Dunner, LLP

(57) ABSTRACT

Novel oxidation bases comprising a benzene nucleus and a guanidine chain, a process for their preparation, their use for the oxidation dyeing of keratin fibers, dye compositions containing them, and oxidation dyeing processes using them are described.

56 Claims, No Drawings

OXIDATION BASES CONTAINING A GUANIDINE CHAIN, PROCESS FOR PREPARING THEM, THEIR USE FOR THE OXIDATION DYEING OF KERATIN FIBERS, DYE COMPOSITIONS AND DYEING PROCESSES

The present invention relates to novel oxidation bases containing a benzene nucleus and comprising a guanidine chain, to a process for their preparation, to their use for the oxidation dyeing of keratin fibers, to dye compositions containing them and to oxidation dyeing processes using them.

It is known practice to dye keratin fibers, and in particular human hair, with dye compositions containing oxidation dye precursors, in particular ortho-phenylenediamines, para-phenylenediamines, ortho-aminophenols or para-aminophenols and heterocyclic compounds, which are generally referred to as oxidation bases. The oxidation dye precursors, or oxidation bases, are colorless or weakly colored compounds which, when combined with oxidizing products, can give rise to colored compounds and dyes by a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds.

The variety of molecules used as oxidation bases and couplers makes it possible to obtain a wide range of colors.

The so-called "permanent" coloration obtained by means of these oxidation dyes should generally satisfy a certain number of requirements. For example, it should have no toxicological drawbacks and it should allow shades of the desired color strength to be obtained and have good resistance to external agents, such as light, bad weather, washing, permanent-waving, perspiration and friction.

The dyes should also allow white hairs to be covered, and, lastly, they should be as unselective as possible, i.e., they should allow the smallest possible differences in coloration to be produced over the entire length of the same keratin fiber, which may indeed be differently sensitized (i.e., damaged) between its end and its root.

Many patents disclosing novel hair dyes containing a benzene nucleus have been published in the literature. Among the most recent, mention may be made, in particular, of the pyrrolidine derivatives disclosed in U.S. Pat. No. 5,851,237, the polyol derivatives disclosed in Japanese patent application no. JP 11-158 046 or piperazine derivatives, such as those disclosed in German patent application no. DE 197 28 335.

However, in the field of oxidation dyes, the dyeing properties such as the remanence with respect to the various attacking factors and the various treatments to which keratin fibers may be subjected, and also the variety of shades obtained after reaction with various couplers, still remain to be improved.

The inventors have now discovered, entirely surprisingly and unexpectedly, that novel compounds containing a benzene nucleus comprising a guanidine chain, of formula (I) defined below, are not only suitable for use as oxidation bases, but also make it possible to obtain dye compositions which give intense colorations, over a broad range of colors, and have excellent properties of fastness (remanence) to the various treatments to which keratin fibers may be subjected. This remanence is significantly greater than that generally of the prior art.

These discoveries form the basis of the present invention.

A first subject of the invention is thus novel compounds of formula (I) below, and the addition salts thereof with an acid:

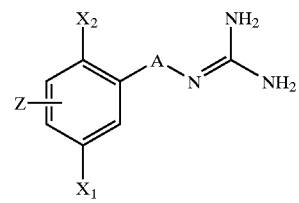

(I)

wherein:
$X_1$ and $X_2$ are each independently chosen from a hydroxyl group, —$NHR_1$ groups and —$NR_1R_2$ groups, wherein $X_1$ and $X_2$ are not simultaneously both hydroxyl groups;

$R_1$ and $R_2$, which may be identical or different, are each chosen from hydrogen atoms, $C_1$–$C_8$ alkyl groups, $C_1$–$C_8$ monohydroxyalkyl groups, $C_2$–$C_8$ polyhydroxyalkyl groups, $C_2$–$C_8$ aminoalkyl groups, mono($C_1$–$C_4$)alkylamino($C_1$–$C_4$)alkyl groups, di($C_1$–$C_4$)alkylamino($C_1$–$C_4$)alkyl groups and $C_1$–$C_8$ haloalkyl groups; when either $X_1$ or $X_2$ represents a group —$NR_1R_2$, then $R_1$ and $R_2$ can optionally form together, in combination with the nitrogen atom to which they are attached, an aromatic or non-aromatic 4-, 5- or 6-membered ring;

$R_1$ and $R_2$, are each independently chosen from aromatic 4-, 5- and 6-membered rings and non-aromatic 4-, 5- and 6-membered rings, wherein said rings may comprise at least one heteroatom;

A is a divalent group chosen from —CH=N— and —$CH_2$—NH—;

Z is a group chosen from a hydrogen atom, a halogen atom, aromatic 4-, 5- and 6-membered rings, non-aromatic 4-, 5- and 6-membered rings, $C_1$–$C_8$ alkyl groups, $C_1$–$C_8$ monohydroxyalkyl groups, $C_2$–$C_8$ polyhydroxyalkyl groups, $C_2$–$C_8$ aminoalkyl groups, mono ($C_1$–$C_4$)alkylamino($C_1$–$C_4$)alkyl groups, di($C_1$–$C_4$) alkylamino($C_1$–$C_4$)alkyl groups, $C_1$–$C_8$ haloalkyl groups, and —$BR_3$ groups wherein B is a divalent group chosen from the following groups:

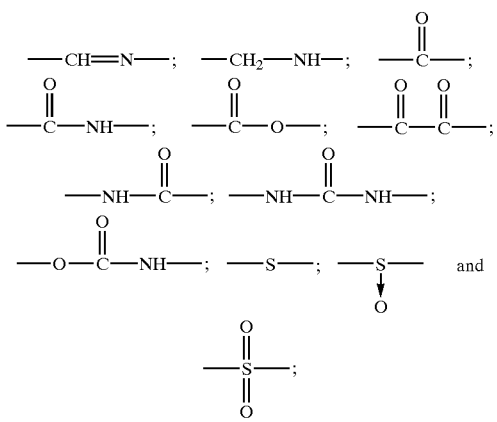

and wherein $R_3$ is chosen from $C_1$–$C_8$ alkyl groups, $C_1$–$C_8$ monohydroxyalkyl groups, $C_2$–$C_8$ polyhydroxyalkyl groups, $C_2$–$C_8$ aminoalkyl groups, mono($C_1$–$C_4$)alkylamino($C_1$–$C_4$)alkyl groups, di($C_1$–$C_4$)alkylamino($C_1$–$C_4$)alkyl groups and $C_1$–$C_8$ haloalkyl groups.

As indicated above, the dyes obtained with the compound(s) of formula (I) in accordance with the invention are powerful and make it possible to obtain a wide range of colors. Furthermore, they have excellent fastness properties with respect to the action of various external agents, such as light, bad weather, washing, permanent-waving, perspiration and friction.

In formula (I) above, the alkyl groups are chosen from linear groups and branched groups.

In formula (I) above, when $R_1$ and $R_2$ form, together with the nitrogen atom to which they are attached, a 4-, 5- or 6-membered ring, or when $R_1$ and/or $R_2$ represent a 4-, 5- or 6-membered ring, or when Z is an aromatic or non-aromatic 4-, 5- or 6-membered ring, then the said rings may bear one or more substituents which may be chosen, for example, from the following groups: hydroxyl groups, amido groups, halogen atoms, cyano groups, $C_1$–$C_8$ alkyl groups, aromatic $C_4$, $C_5$ and $C_6$ rings and non-aromatic $C_4$, $C_5$ and $C_6$ rings.

Embodiments of compounds of formula (I) include the following compounds:

5-amino-2-hydroxy-benzylideneamino-guanidine,
2-amino-5-hydroxy-benzylideneamino-guanidine,
2,5-diamino-benzylideneamino-guanidine,
5-dihydroxyethylamino-2-hydroxy-benzylideneamino-guanidine,
5-dimethylamino-2-hydroxy-benzylideneamino-guanidine,
2-dihydroxyethylamino-5-hydroxy-benzylideneamino-guanidine,
2-dimethylamino-5-hydroxy-benzylideneamino-guanidine,
2-dihydroxyethylamino-5-amino-benzylideneamino-guanidine,
5-dihydroxyethylamino-2-amino-benzylideneamino-guanidine,
5-dimethylamino-2-amino-benzylideneamino-guanidine,
2-dimethylamino-5-amino-benzylideneamino-guanidine,
2-N-pyrrolidinyl-5-amino-benzylideneamino-guanidine,
5-N-pyrrolidinyl-2-amino-benzylideneamino-guanidine,
and the addition salts thereof with an acid.

The addition salts with an acid of the compounds of formula (I) in accordance with the invention (mono- or disalification) may be chosen from inorganic salts and organic salts, such as hydrochlorides, hydrobromides, sulphates, citrates, succinates, tartrates, lactates and acetates. For example, the addition salt may be chosen from the hydrochloride salts.

A subject of the invention is also a process for preparing the compounds of formula (I) in accordance with the invention, which comprises carrying out a direct coupling of the aminoguanidine with a benzaldehyde derivative whose substituents correspond to the compound of formula (I) which can be obtained, in an organic solvent such as an alcohol, to for instance ethanol, at a temperature ranging from 10° C. to the reflux temperature of said solvent. Said coupling may be followed by other reactions, for example a conventional reduction of a nitro group or a reduction of an imine function, leading to the expected compounds of formula (I). More details are given in the experimental section below.

When the synthesis is complete, the compounds of formula (I) in accordance with the invention may, if necessary, be recovered by methods that are well known in the prior art, such as crystallization or distillation.

Another subject of the invention is the use of the compounds of formula (I) in accordance with the invention as oxidation bases for the oxidation dyeing of keratin fibers, for example of human keratin fibers such as hair.

A subject of the invention is also a composition for the oxidation dyeing of keratin fibers, for example of human keratin fibers such as hair, wherein said composition comprises, as an oxidation base, in a medium which is suitable for dyeing, at least one compound of formula (I) in accordance with the invention.

The compound of formula (I) in accordance with the invention may be present at a concentration ranging from 0.0005% to 12% by weight approximately relative to the total weight of the dye composition, for example from 0.005% to 6% by weight approximately relative to this weight.

The medium which is suitable for dyeing and the medium which is suitable for support generally comprises water or a mixture of water and at least one organic solvent to dissolve the compounds which would not be sufficiently soluble in water. Examples of organic solvents include, for example, $C_1$–$C_4$ lower alkanols such as ethanol and to isopropanol; glycerol; glycols and glycol ethers such as 2-butoxyethanol, propylene glycol, propylene glycol monomethyl ether, diethylene glycol monoethyl ether and monomethyl ether; aromatic alcohols such as benzyl alcohol or phenoxyethanol; and similar products and mixtures thereof.

The solvents can be present in proportions generally ranging from 1% to 40% by weight approximately relative to the total weight of the dye composition, for example from 5% to 30% by weight approximately.

The pH of the dye composition in accordance with the invention generally ranges from 3 to 12, approximately, for example from 5 to 11, approximately. It can be adjusted to the desired value using acidifying or basifying agents commonly used to dye keratin fibers.

Examples of acidifying agents which may be used, include, for example, inorganic acids and organic acids such as hydrochloric acid, orthophosphoric acid, sulphuric acid, carboxylic acids such as acetic acid, tartaric acid, citric acid and lactic acid, and sulphonic acids.

Examples of basifying agents which can be used, include, for example, aqueous ammonia, alkaline carbonates, alkanolamines such as mono-, di- and triethanolamine and derivatives thereof, sodium hydroxide, potassium hydroxide and compounds of formula (II) below:

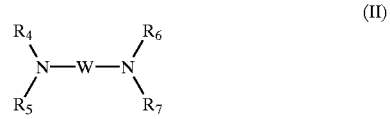

(II)

wherein W is a propylene residue optionally substituted with at least one group chosen from hydroxyl groups and $C_1$–$C_6$ alkyl groups; $R_4$, $R_5$, $R_6$ and $R_7$, which may be identical or different, are each chosen from hydrogen atoms, $C_1$–$C_6$ alkyl groups and $C_1$–$C_6$ hydroxyalkyl groups.

In addition to the at least one compound of formula (I) defined above, the dye composition in accordance with the invention may also contain at least one additional oxidation base which may be chosen from oxidation bases conventionally used in oxidation dyeing, including, for example, para-phenylenediamines other than the compounds of formula (I), bis(phenyl)alkylenediamines, para-aminophenols other than the compounds of formula (I), ortho-aminophenols and heterocyclic bases.

Examples of para-phenylenediamines include, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,y-dihydroxypropyl)-para-phenylenediamine, N(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N-(β-methoxyethyl)-para-phenylenediamine, and the addition salts thereof with an acid.

Embodiments of the invention may accordingly employ para-phenylenediamines including, for example, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid.

Examples of bis(phenyl)alkylenediamines include, for example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'methylphenyl)ethylenediamine and 1,8-bis(2,5-diaminophenoxy)-3,5-dioxaoctane, and the addition salts thereof with an acid.

Examples of para-aminophenols include, for example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Examples of ortho-aminophenols include, for example, 2-aminophenol, 2-amino-5-methylphenol, 2-amino-6-methylphenol and 5-acetamido-2-aminophenol, and the addition salts thereof with an acid.

Examples of heterocyclic bases include, for example, pyridine derivatives, pyrimidine derivatives and pyrazole derivatives.

Examples of pyridine derivatives include, for example, those described in Great Britain patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Examples of pyrimidine derivatives include, for example, those described in German patent DE 2 359 399, Japanese patents JP 88-169 571 and JP 05 163 12, European patent EP 0 770 375, and International patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in French patent application FR-A-2 750 048 including pyrazolo[1,5-a]pyrimidine-3,7-diamine; 2,5-dimethylpyrazolo[1,5-a]pyrimidine-3,7-pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine and 2,5, N7,N7-tetramethylpyrazolo[1,5-a]pyrimidine-3,7-diamine and 3-amino-5-methyl-7-imidazolylpropylaminopyrazolo[1,5-a]pyrimidine, and the addition salts thereof with an acid and the tautomeric forms thereof, when a tautomeric equilibrium exists.

Examples of pyrazole derivatives include those described in patents German DE 3 843 892 and DE 4 133 95, International patent applications WO 94/08969, and WO 94/08970, French patent application FR-A-2 733 749 and German patent application DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

When they are used, these additional oxidation bases generally represent a concentration ranging from 0.0005% to 12% by weight approximately relative to the total weight of the dye composition, for example, from 0.005% to 6% by weight approximately relative to this weight.

The oxidation dye compositions in accordance with the invention can optionally comprise at least one component chosen from couplers and direct dyes, for example to modify the shades or to enrich them with glints.

The couplers which may be used in the oxidation dye compositions in accordance with the invention may be chosen from couplers used conventionally in oxidation dyeing such as, for example, meta-phenylenediamines, meta-aminophenols, meta-diphenols and heterocyclic couplers such as, for example, indole derivatives, indolene derivatives, pyridine derivatives and pyrazolones, and the addition salts thereof with an acid.

Examples of these couplers include 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 2-methyl-1-naphthol, 6-hydroxyindole, 4-hydroxyindole, 4-hydroxy-N-methylindole, 6-hydroxyindoline, 6-hydroxybenzomorpholine, 2,6-dihydroxy-4-methylpyridine, 1H-3-methylpyrazol-5-one and 1-phenyl-3-methylpyrazol-5-one, and the addition salts thereof with an acid.

When they are present, the coupler(s) generally are present at a concentration ranging from 0.0001% to 10% by weight approximately relative to the total weight of the dye composition, for example, from 0.005% to 5% by weight approximately relative to this weight.

In general, the addition salts with an acid which can be used in the context of the dye compositions of the invention (compounds of formula (I), additional oxidation bases and couplers) include, for example, hydrochlorides, hydrobromides, sulphates, citrates, succinates, tartrates, lactates and acetates.

The dye composition in accordance with the invention can optionally comprise at least one of various adjuvants conventionally used in compositions for dyeing the hair, such as anionic surfactants, cationic surfactants, nonionic surfactants, amphoteric surfactants, zwitterionic surfactants, anionic polymers, cationic polymers, nonionic polymers, amphoteric polymers, zwitterionic polymers, inorganic thickeners, organic thickeners, antioxidants, penetration agents, sequestering agents, fragrances, buffers, dispersing agents, and packaging agents such as, for example, silicones, film-forming agents, preserving agents and opacifiers.

Accordingly, a person skilled in the art will take care to select these optional additional compounds such that the advantageous properties intrinsically associated with the oxidation dye composition in accordance with the invention are not, or are not substantially, adversely affected by the addition(s) envisaged.

The dye composition according to the invention can be in various forms, such as in liquid form, cream form, gel form and in any other form which is suitable for dyeing keratin fibers, including human hair.

The invention also relates to a process for the dyeing of keratin fibers, including human keratin fibers such as hair, using the dye composition as defined above.

According to this process, at least one dye composition as defined above is applied to the fibers, the color being developed at a pH chosen from acidic, neutral and alkaline using an oxidizing agent which is added to the dye composition just at the time of use, or which is present in an oxidizing composition which is applied separately, simultaneously or sequentially.

According to one embodiment of the dyeing process of the invention, the dye composition described above may be mixed, at the time of use, with an oxidizing composition comprising, in a medium which is suitable for dyeing, at least one oxidizing agent present in an amount which is sufficient to develop a coloration. The mixture obtained is then applied to the keratin fibers and is left in place for a time period ranging from 3 to 50 minutes approximately, for example from 5 to 30 minutes approximately, after which the fibers are rinsed, and optionally washed with shampoo, rinsed again and dried.

The oxidizing agent can be chosen from oxidizing agents conventionally used for the oxidation dyeing of keratin fibers, including hydrogen peroxide, urea peroxide, alkali metal bromates and persalts such as perborates and persulphates, peracids, and enzymes, for example, peroxidases, 2-electron oxidoreductases such as uricases, and 4-electron oxygenases such as laccases. In one embodiment, the oxidizing agent is hydrogen peroxide.

The pH of the oxidizing composition comprising the oxidizing agent as defined above is such that, after mixing with the dye composition, the pH of the resultant composition applied to the keratin fibers generally ranges from 3 to 12 approximately, for example from 5 to 11. It is adjusted to the desired value using at least one acidifying or basifying agent commonly used to dye keratin fibers and as defined above.

The oxidizing composition as defined above can optionally comprise at least one of various adjuvants conventionally used in compositions for dyeing the hair and as defined above.

The composition which is finally applied to the keratin fibers can be in various forms, such as in the form of liquids, creams, gels and any other form which is suitable for dyeing keratin fibers, including human hair.

Another subject of the invention is a multi-compartment dyeing device or "kit" or any other multi-compartment packaging system, comprising a first compartment comprising a dye composition as defined above and a second compartment comprising an oxidizing composition as defined above. These devices can be equipped with a means for delivering the desired mixture onto hair, such as devices described in French patent application no. FR-2,586,913 in the name of L'Oréal The following examples are intended to illustrate the invention without limiting the scope thereof.

PREPARATION EXAMPLES

Preparation Example 1

Synthesis of 5-amino-2-hydroxy-benzylideneamino-guanidine Dihydrochloride

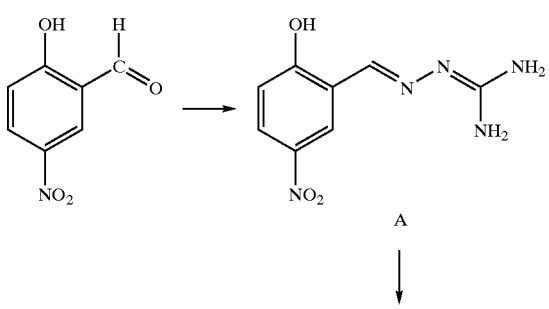

A

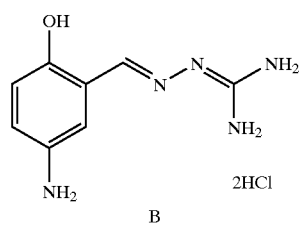

a) Preparation of 2-hydroxy-5-nitro-benzylideneamino-guanidine Monohydrate (A).

9 g (53.85 mmol) of 2-hydroxy-5-nitrobenzaldehyde were dissolved in 200 ml of ethanol in a 500 ml reactor. 5.95 g (53.85 mmol) of aminoguanidine hydrochloride and 7.6 ml of triethylamine were then introduced. The homogeneous mixture was heated at 45° C. for 3 hours. A yellow precipitate formed. After filtration, washing with water and acetone, and then drying under vacuum over phosphorus pentoxide, 12 g of a pale yellow solid were obtained in a final yield of monohydrate of 92%.

Melting point: greater than 140° C. Elemental analysis calculated for $C_8H_9N_5O_3 \cdot H_2O$:

| % | C | H | N | O |
|---|---|---|---|---|
| Calculated | 39.80 | 4.56 | 29.02 | 26.53 |
| Found | 39.51 | 4.82 | 28.38 | 25.15 | b) Preparation of 5-amino-2-hydroxy-benzylideneamino-guanidine Dihydrochloride (B)

Compound A obtained above in the preceding step (30 g, 134.4 mmol) was suspended in 600 ml of ethanol in the presence of dry palladium-on-charcoal, and was then hydrogenated under 15 bar at a temperature of 40° C.–60° C. The mixture was filtered under nitrogen and then recovered in an ice-cold hydrochloric ethanol solution. After crystallization, filtration, washing with ethyl ether and then drying under vacuum, 9.9 g of a white solid were obtained in a final yield of 28%, which melted at 215° C. and the elemental analysis of which, calculated for $C_8H_{11}N_5O_5 \cdot 2HCl \cdot 1H_2O$, was:

| % | C | H | N | O | Cl |
|---|---|---|---|---|---|
| Calculated | 33.79 | 5.27 | 24.64 | 11.26 | 24.99 |
| Found | 34.35 | 5.24 | 24.88 | 10.06 | 25.38 |

Preparation Example 2

Synthesis of 2-amino-5-hydroxy-benzylideneamino-guanidine Dihydrochloride

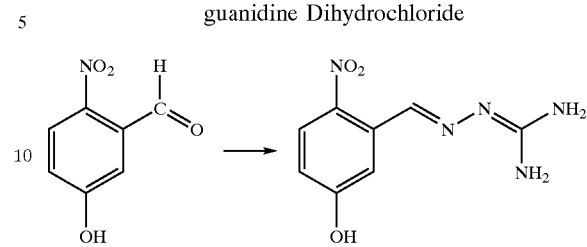

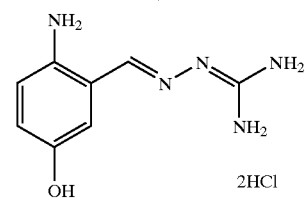

a) Preparation of 5-hydroxy-2-nitro-benzylideneamino-guanidine Monohydrate (A')

4.8 g (28.7 mmol) of 5-hydroxy-2-nitrobenzaldehyde were dissolved in 40 ml of methanol in a 100 ml reactor. 3.2 g (28.7 mmol) of aminoguanidine hydrochloride and 4 ml of triethylamine were then introduced. The homogeneous mixture was heated at a temperature of 45–50° C. for about 24 hours. A yellow precipitate formed. After filtration, washing with water and acetone, and then drying under vacuum over phosphorus pentoxide, 5.5 g of a pale yellow solid were obtained in a final yield of 85%.

The elemental analysis calculated for $C_8H_9N_5O_3$ was:

| % | C | H | N | O |
|---|---|---|---|---|
| Calculated | 43.05 | 4.06 | 31.38 | 21.51 |
| Found | 42.64 | 3.91 | 30.67 | 21.82 | b) Preparation of 2-amino-5-hydroxy-benzylideneamino-guanidine Dihydrochloride (B')

The nitro compound A' obtained above in the preceding step (3 g, 13.4 mmol) was reduced according to the method described above in Example 1, step b), by catalytic hydrogenation under a pressure of 15 bar at a temperature of 40° C., to give 2 g (56%) of compound B'.

The elemental analysis calculated for $C_8H_{11}N_5O \cdot 2HCl$ was:

| % | C | H | N | O | Cl |
|---|---|---|---|---|---|
| Calculated | 36.11 | 4.92 | 26.32 | 6.01 | 26.64 |
| Found | 35.86 | 4.94 | 26.05 | 7.62 | 26.37 |

Examples 1 to 6 of Dyeing in Basic Medium

The dye compositions below were prepared (contents in grams):

| | EXAMPLE | | | | | |
|---|---|---|---|---|---|---|
| | 1 | 2 | 3 | 4 | 5 | 6 |
| 5-Amino-2-hydroxy-benzylimino-guanidine dihydrochloride (compound of formula (I)) | 0.798 | 0.798 | 0.798 | 0.798 | 0.798 | 0.798 |
| 6-Hydroxybenzomorpholine (Coupler) | 0.453 | — | — | — | — | — |
| 2,4-Diamino-1-(β-hydroxy-ethyloxy)benzene dihydrochloride (Coupler) | — | 0.723 | — | — | — | — |
| 1,3-Dihydroxybenzene (Coupler) | — | — | 0.33 | — | — | — |
| 3-Aminophenol (Coupler) | — | — | — | 0.327 | — | — |
| 1,3-Dihydroxy-2-methyl-benzene (Coupler) | — | — | — | — | 0.372 | — |
| 5-N-(β-Hydroxyethyl)amino-2-methylphenol (Coupler) | — | — | — | — | — | — |
| Common dye support | (*) | (*) | (*) | (*) | (*) | (*) |
| Demineralized water qs | 100 g | 100 g | 100 g | 100 g | 100 g | 100 g |

(*) Common dye support:

| | |
|---|---|
| Benzyl alcohol | 2 g |
| Polyethylene glycol 6 EO | 3 g |
| Ethanol | 18 g |
| ($C_8$–$C_{10}$)alkyl polyglucoside as an aqueous solution containing 60% active material, buffered with ammonium citrate, sold under the name Oramix CG110 by SEPPIC | 5 g |
| Aqueous ammonia containing 20% $NH_3$ | 10 g |
| Sodium metabisulphite | 0.205 g |
| Sequestering agent | qs |

At the time of use, each of the dye compositions above was mixed weight-for-weight with a 20-volumes hydrogen peroxide solution (6% by weight) of pH 3.

The mixture obtained was applied to locks of natural grey hair containing 90% white hairs, for 30 minutes. The locks were then rinsed, washed with a standard shampoo, rinsed again and then dried.

The shades obtained are given in the table below:

| EXAMPLE | DYEING pH | Shade on natural hair |
|---|---|---|
| 1 | 10 ± 0.2 | mahogany golden dark blonde |
| 2 | 10 ± 0.2 | iridescent ash chestnut |
| 3 | 10 ± 0.2 | matt golden dark blonde |
| 4 | 10 ± 0.2 | ash mahogany blonde |
| 5 | 10 ± 0.2 | mahogany |
| 6 | 10 ± 0.2 | coppery dark blonde |

What is claimed is:

1. An acid addition salt of a compound of formula (1),

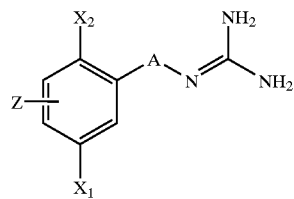

(I)

wherein:
$X_1$ and $X_2$, which may be identical or different, are each independently chosen from hydroxyl groups, —$NHR_1$ groups, and —$NR_1R_2$ groups, provided that $X_1$ and $X_2$ are not simultaneously a hydroxyl group;

$R_1$ and $R_2$, which may be identical or different, are each independently chosen from hydrogen atoms, $C_1$–$C_8$ alkyl groups, $C_1$–$C_8$ monohydroxyalkyl groups, $C_2$–$C_8$ polyhydroxyalkyl groups, $C_2$–$C_8$ aminoalkyl groups, mono($C_1$–$C_4$)alkylamino($C_1$–$C_4$)alkyl groups, di($C_1$–$C_4$)alkylamino($C_1$–$C_4$)alkyl groups and $C_1$–$C_8$ haloalkyl groups; wherein when at least one group chosen from $X_1$ and $X_2$ is a —$NR_1R_2$ group, then $R_1$ and $R_2$ of said —$NR_1R_2$ group may form, together with the nitrogen atom to which they are attached, a ring structure chosen from aromatic 4-, 5- and 6-membered rings and non-aromatic 4-, 5- and 6-membered rings;

$R_1$ and $R_2$, which may be identical or different, may also independently be chosen from aromatic 4-, 5- and 6-membered rings and non-aromatic 4-, 5- and 6-membered rings, wherein said rings may comprise at least one heteroatom;

A is a divalent group chosen from —CH=N— and —$CH_2$—NH—;

Z is a group chosen from a hydrogen atom, a halogen atom, aromatic 4-, 5- and 6-membered rings, non-aromatic 4-, 5- and 6-membered rings, $C_1$–$C_8$ alkyl groups, $C_1$–$C_8$ monohydroxyalkyl groups, $C_2$–$C_8$ polyhydroxyalkyl groups, $C_2$–$C_8$ aminoalkyl groups, mono($C_1$–$C_4$)alkylamino($C_1$–$C_4$)alkyl groups, di($C_1$–$C_4$)alkylamino($C_1$–$C_4$)alkyl groups, $C_1$–$C_8$ haloalkyl groups, cyano groups and —$BR_3$ groups wherein B is a divalent group chosen from the groups:

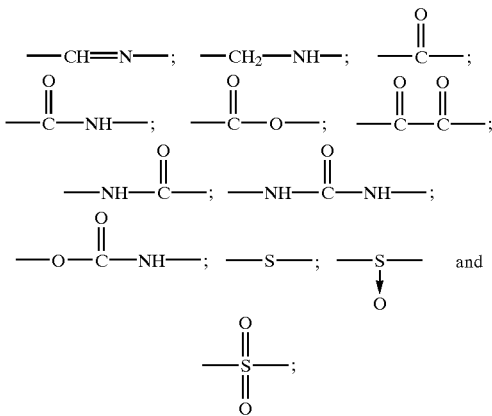

and wherein $R_3$ is chosen from $C_1$–$C_8$ alkyl groups, $C_1$–$C_8$ monohydroxyalkyl groups, $C_2$–$C_8$ polyhydroxyalkyl groups, $C_2$–$C_8$ aminoalkyl groups, mono($C_1$–$C_4$)alkylamino($C_1$–$C_4$)alkyl groups, di($C_1$–$C_4$)alkylamino($C_1$–$C_4$)alkyl groups and $C_1$–$C_8$ haloalkyl groups; and with the proviso that when A is —CH=N—, $X_1$ is —$NHR_1$ wherein $R_1$ is a hydrogen atom, and $X_2$ is —$NR_1R_2$ wherein $R_1$ and $R_2$ of said —$NR_1R_2$ group form, together with the nitrogen atom to which they are attached, a ring structure chosen from non-aromatic 6-membered rings, and said non-aromatic 6-membered rings are chosen from piperazine and piperidine, then Z is not a hydrogen atom; and wherein the acid addition salt of the compounds of formula (I) is chosen from hydrochlorides, hydrobromides, sulphates, citrates, succinates, tartrates, lactates and acetates.

2. A composition comprising at least one compound of formula (I), or an acid addition salt thereof,

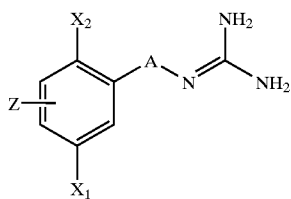

wherein:
- $X_1$ and $X_2$, which may be identical or different, are each independently chosen from hydroxyl groups, —$NHR_1$ groups, and —$NR_1R_2$ groups, provided that $X_1$ and $X_2$ are not simultaneously a hydroxyl group;
- $R_1$ and $R_2$, which may be identical or different, are each independently chosen from hydrogen atoms, $C_1$–$C_8$ alkyl groups, $C_1$–$C_8$ monohydroxyalkyl groups, $C_2$–$C_8$ polyhydroxyalkyl groups, $C_2$–$C_8$ aminoalkyl groups, mono($C_1$–$C_4$)alkylamino($C_1$–$C_4$)alkyl groups, di($C_1$–$C_4$)alkylamino($C_1$–$C_4$)alkyl groups and $C_1$–$C_8$ haloalkyl groups; wherein when at least one group chosen from $X_1$ and $X_2$ is a —$NR_1R_2$ group, then $R_1$ and $R_2$ of said —$NR_1R_2$ group may form, together with the nitrogen atom to which they are attached, a ring structure chosen from aromatic 4-, 5- and 6-membered rings and non-aromatic 4-, 5- and 6-membered rings;
- $R_1$ and $R_2$, which may be identical or different, may also independently be chosen from aromatic 4-, 5- and 6-membered rings and non-aromatic 4-, 5- and 6-membered rings, wherein said rings may comprise at least one heteroatom;
- A is a divalent group chosen from —CH=N— and —$CH_2$—NH—;
- Z is a group chosen from a hydrogen atom, a halogen atom, aromatic 4-, 5- and 6-membered rings, non-aromatic 4-, 5- and 6-membered rings, $C_1$–$C_8$ alkyl groups, $C_1$–$C_8$ monohydroxyalkyl groups, $C_2$–$C_8$ polyhydroxyalkyl groups, $C_2$–$C_8$ aminoalkyl groups, mono($C_1$–$C_4$)alkylamino($C_1$–$C_4$)alkyl groups, di($C_1$–$C_4$)alkylamino($C_1$–$C_4$)alkyl groups, $C_1$–$C_8$ haloalkyl groups, cyano groups and —$BR_3$ groups wherein B is a divalent group chosen from the groups:

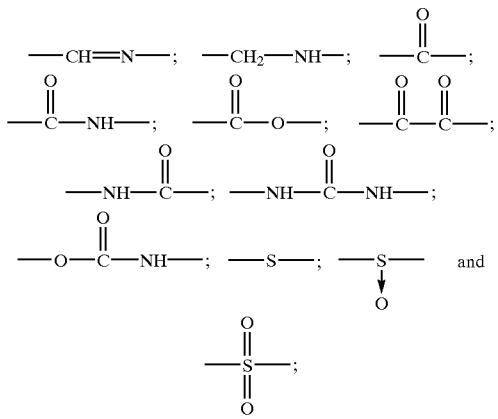

and wherein $R_3$ is chosen from $C_1$–$C_8$ alkyl groups, $C_1$–$C_8$ monohydroxyalkyl groups, $C_2$–$C_8$ polyhydroxyalkyl groups, $C_2$–$C_8$ aminoalkyl groups, mono($C_1$–$C_4$)alkylamino ($C_1$–$C_4$)alkyl groups, di($C_1$–$C_4$)alkylamino($C_1$–$C_4$)alkyl groups and $C_1$–$C_8$ haloalkyl groups; and
wherein said at least one compound of formula (I) or acid addition salt thereof is present in said composition in an amount effective for dyeing keratin fibers.

3. A composition according to claim 2, in a form suitable for dyeing at least one keratin fiber chosen from liquid form, cream form and gel form.

4. A composition according to claim 2, further comprising a medium which is suitable for dyeing at least one keratin fiber chosen from water and a mixture of water and at least one organic solvent.

5. A composition according to claim 2, wherein the compound of formula (I) is present at a concentration ranging from 0.0005% to 12% by weight relative to the total weight of the dye composition.

6. A composition according to claim 5, wherein said concentration ranges from 0.005% to 6% by weight relative to the total weight of the dye composition.

7. A composition according to claim 2, wherein, in addition to the compound of formula (I), said composition further comprises at least one additional oxidation base.

8. A composition according to claim 7, wherein said at least one additional oxidation base is chosen from para-phenylenediamines other than a compound of formula(I), bis(phenyl)alkylenediamines, para-aminophenols other than a compound of formula (I), ortho-aminophenols and heterocyclic bases.

9. A composition according to claim 8, wherein the para-phenylenediamines are chosen from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-phydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N-(β-methoxyethyl)-para-phenylenediamine, and the acid addition salts thereof.

10. A composition according to claim 8, wherein the bis(phenyl)alkylenediamines are chosen from N,N'-bis(β-hydroxyethyl)-N,N'-bis(4'-aminophenyl)-1,3-diaminopropanol, N,N'-bis(β-hydroxyethyl)-N,N'-bis (4'aminophenyl)ethylenediamine, N,N'-bis(4-aminophenyl) tetramethylenediamine, N,N'-bis(β-hydroxyethyl)-N,N'-bis (4-aminophenyl)tetramethylenediamine, N,N'-bis(4-methylaminophenyl)tetramethylenediamine, N,N'-bis (ethyl)-N,N'-bis(4'-amino-3'-methylphenyl)ethylenediamine and 1,8-bis(2,5-diaminophenoxy)-3,5-dioxaoctane, and the acid addition salts thereof.

11. A composition according to claim 8, wherein the para-aminophenols are chosen from para-aminophenol, 4-amino-3-methylphenol, 4-amino-3-fluorophenol, 4-amino-3-hydroxymethylphenol, 4-amino-2- methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid addition salts thereof.

12. A composition according to claim 8, wherein the heterocyclic bases are chosen from pyridine derivatives, pyrimidine derivatives and pyrazole derivatives.

13. A composition according to claim 7, wherein said at least one additional oxidation base is present at a concentration ranging from 0.0005% to 12% by weight relative to the total weight of the dye composition.

14. A composition according to claim 13, wherein said concentration ranges from 0.005% to 6% by weight relative to the total weight of the dye composition.

15. A composition according to claim 2, further comprising at least one component chosen from couplers and direct dyes.

16. A composition according to claim 15, wherein said couplers are chosen from meta-phenylenediamines, meta-aminophenols, meta-diphenols and heterocyclic couplers.

17. A composition according to claim 16, wherein said couplers are chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 2-methyl-1-naphthol, 6-hydroxyindole, 4-hydroxyindole, 4-hydroxy-N-methylindole, 6-hydroxyindoline, 6-hydroxybenzomorpholine, 2,6-dihydroxy-4-methylpyridine, 1H-3-methylpyrazol-5-one and 1-phenyl-3-methylpyrazol-5-one, and the acid addition salts thereof.

18. A composition according to claim 15, wherein said coupler is present at a concentration ranging from 0.0001% to 10% by weight relative to the total weight of the dye composition.

19. A composition according to claim 18, wherein said concentration ranges from 0.005% to 5% by weight relative to the total weight of the dye composition.

20. A composition according to claim 2, wherein said acid addition salts are chosen from hydrochlorides, hydrobromides, sulphates, citrates, succinates, tartrates, lactates and acetates.

21. A composition according to claim 2, further comprising at least one adjuvant chosen from anionic surfactants, cationic surfactants, nonionic surfactants, amphoteric surfactants, zwitterionic surfactants, anionic polymers, cationic polymers, nonionic polymers, amphoteric polymers, zwitterionic polymers, inorganic thickeners, organic thickeners, antioxidants, penetration agents, sequestering agents, fragrances, buffers, dispersing agents, packaging agents, silicones, film-forming agents, preserving agents and opacifiers.

22. A composition according to claim 2, further comprising at least one agent chosen from acidifying agents and basifying agents.

23. A process for oxidation dyeing of keratin fibers, comprising applying to said keratin fibers at least one dye composition comprising, in a medium appropriate for dyeing, at least one compound of formula (I), or an acid addition salt thereof,

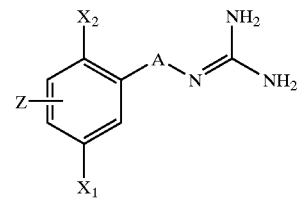

(I)

wherein:
$X_1$ and $X_2$, which may be identical or different, are each independently chosen from hydroxyl groups, —$NHR_1$ groups, and —$NR_1R_2$ groups, provided that $X_1$ and $X_2$ are not simultaneously a hydroxyl group;

$R_1$ and $R_2$ which may be identical or different, are each independently chosen from hydrogen atoms, $C_1$–$C_8$ alkyl groups, $C_1$–$C_8$ monohydroxyalkyl groups, $C_2$–$C_8$ polyhydroxyalkyl groups, $C_2$–$C_8$ aminoalkyl groups, mono($C_1$–$C_4$)alkylamino($C_1$–$C_4$)alkyl groups, di($C_1$–$C_4$)alkylamino($C_1$–$C_4$)alkyl groups and $C_1$–$C_8$ haloalkyl groups; wherein when at least one group chosen from $X_1$ and $X_2$ is a —$NR_1R_2$ group, then $R_1$ and $R_2$ of said —$NR_1R_2$ group may form, together with the nitrogen atom to which they are attached, a ring structure chosen from aromatic 4-, 5- and 6-membered rings and non-aromatic 4-, 5- and 6-membered rings;

$R_1$ and $R_2$, which may be identical or different, may also independently be chosen from aromatic 4-, 5- and 6-membered rings and non-aromatic 4-, 5- and 6-membered rings, wherein said rings may comprise at least one heteroatom;

A is a divalent group chosen from —CH=N— and —CH$_2$—NH—;

Z is a group chosen from a hydrogen atom, a halogen atom, aromatic 4-, 5- and 6-membered rings, non-aromatic 4-, 5- and 6-membered rings, $C_1$–$C_8$ alkyl groups, $C_1$–$C_8$ monohydroxyalkyl groups, $C_2$–$C_8$ polyhydroxyalkyl groups, $C_2$–$C_8$ aminoalkyl groups, mono($C_1$–$C_4$)alkylamino($C_1$–$C_4$)alkyl groups, di($C_1$–$C_4$)alkylamino($C_1$–$C_4$)alkyl groups, $C_1$–$C_8$ haloalkyl groups, cyano groups and —$BR_3$ groups wherein B is a divalent group chosen from the groups:

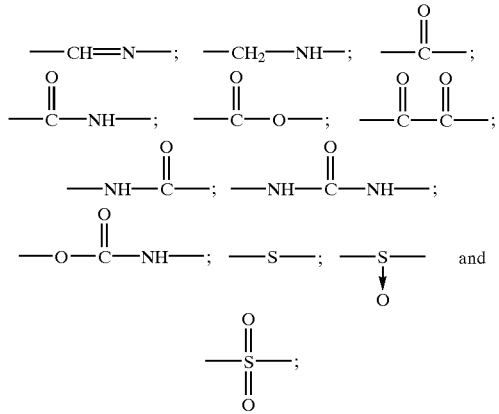

and wherein $R_3$ is chosen from $C_1$–$C_8$ alkyl groups, $C_1$–$C_8$ monohydroxyalkyl groups, $C_2$–$C_8$ polyhydroxyalkyl groups, $C_2$–$C_8$ aminoalkyl groups, mono($C_1$–$C_4$)alkylamino($C_1$–$C_4$)alkyl groups, di($C_1$–$C_4$)alkylamino($C_1$–$C_4$)alkyl groups and $C_1$–$C_8$ haloalkyl groups;

and contacting said dye composition with at least one oxidizing agent.

24. A process according to claim 23, wherein said oxidizing agent is chosen from atmospheric oxygen, hydrogen peroxide, urea peroxide, alkali metal bromates, persalts, peracids and enzymes.

25. A process according to claim 24, wherein said enzymes are chosen from peroxidases, 2-electron oxidoreductases and 4-electron oxygenases.

26. A process according to claim 23, wherein said oxidizing agent is added to the dye composition at the time of application of the dye composition to the keratin fibers.

27. A process according to claim 23, wherein said oxidizing agent is present in an oxidizing composition which is applied to said keratin fibers separately, simultaneously, or sequentially with said dye composition.

28. A process according to claim 23, wherein a color achieved by said oxidation dyeing is revealed at a pH chosen from acidic pH, neutral pH and alkaline pH.

29. A process according to claim 23, wherein following application of said dye composition and contact with said oxidizing agent, said keratin fibers are allowed to remain in place for a time period ranging from 3 to 50 minutes approximately.

30. A process according to claim 29, wherein said time period ranges from 5 to 30 minutes approximately.

31. A process according to claim 29, further comprising rinsing said keratin fibers at least one time and optionally shampooing said rinsed fibers at least one time following application of said dye composition and contact with said oxidizing agent.

32. A process according to claim 23, wherein said keratin fibers are human keratin fibers.

33. A process according to claim 23, wherein said human keratin fibers are hair.

34. A process according to claim 23, wherein the compound of formula (I) is present at a concentration ranging from 0.0005% to 12% by weight relative to the total weight of the dye composition.

35. A process according to claim 34, wherein said concentration ranges from 0.005% to 6% by weight relative to the total weight of the dye composition.

36. A process according to claim 23, wherein, in addition to the compound of formula (I), said dye composition comprises at least one additional oxidation base.

37. A process according to claim 36, wherein said at least one additional oxidation base is chosen from para-phenylenediamines other than a compound of formula(I), bis(phenyl)alkylenediamines, para-aminophenols other than a compound of formula (I), ortho-aminophenols and heterocyclic bases.

38. A process according to claim 37, wherein the para-phenylenediamines are chosen from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-phydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(βhydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N-(β-methoxyethyl)-para-phenylenediamine, and the acid addition salts thereof.

39. A process according to claim 37, wherein the bis (phenyl)alkylenediamines are chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4aminophenyl) tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5 diaminophenoxy)-3,5-dioxaoctane, and the acid addition salts thereof.

40. A process according to claim 37, wherein the para-aminophenols are chosen from para-aminophenol, 4-amino-3-methylphenol, 4-amino-3-fluorophenol, 4-amino-3hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid addition salts thereof.

41. A process according to claim 37, wherein the heterocyclic bases are chosen from pyridine derivatives, pyrimidine derivatives and pyrazole derivatives.

42. A process according to claim 36, wherein said at least one additional oxidation base is present at a concentration ranging from 0.0005% to 12% by weight relative to the total weight of the dye composition.

43. A process according to claim 42, wherein said concentration ranges from 0.005% to 6% by weight relative to the total weight of the dye composition.

44. A process according to claim 23, wherein said at least one dye composition further comprises least one component chosen from couplers and direct dyes.

45. A process according to claim 44, wherein said couplers are chosen from meta-phenylenediamines, meta-aminophenols, meta-diphenols and heterocyclic couplers.

46. A process according to claim 45, wherein said couplers are chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 2-methyl-1-naphthol, 6-hydroxyindole, 4-hydroxyindole, 4-hydroxy-N-methylindole, 6-hydroxyindoline, 6-hydroxybenzomorpholine, 2,6-dihydroxy-4-methylpyridine, 1H-3-methylpyrazol-5-one and 1-phenyl-3-methylpyrazol-5-one, and the acid addition salts thereof.

47. A process according to claim 44, wherein said couplers are present at a concentration ranging from 0.0001% to 10% by weight relative to the total weight of the dye composition.

48. A process according to claim 47, wherein said concentration ranges from 0.005% to 5% by weight relative to the total weight of the dye composition.

49. A process according to claim 23, wherein said acid addition salts of formula (I) are chosen from hydrochlorides, hydrobromides, sulphates, citrates, succinates, tartrates, lactates and acetates.

50. A process according to claim 23, wherein said at least one dye composition further comprises at least one adjuvant chosen from anionic surfactants, cationic surfactants, non-ionic surfactants, amphoteric surfactants, zwitterionic surfactants, anionic polymers, cationic polymers, nonionic polymers, amphoteric polymers, zwitterionic polymers, inorganic thickeners, organic thickeners, antioxidants, penetration agents, sequestering agents, fragrances, buffers, dispersing agents, packaging agents, silicones, film-forming agents, preserving agents and opacifiers.

51. A process according to claim 23, wherein said at least one dye composition further comprises at least one agent chosen from acidifying agents and basifying agents.

52. A process for preparing a compound of formula (I), or an acid addition salt thereof,

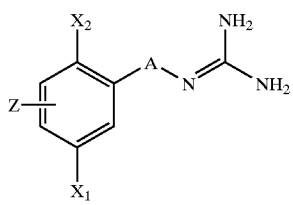

wherein:

$X_1$ and $X_2$, which may be identical or different, are each independently chosen from hydroxyl groups, —$NHR_1$ groups, and —$NR_1R_2$ groups, provided that $X_1$ and $X_2$ are not simultaneously a hydroxyl group;

$R_1$ and $R_2$, which may be identical or different, are each independently chosen from hydrogen atoms, $C_1$–$C_8$ alkyl groups, $C_1$–$C_8$ monohydroxyalkyl groups, $C_2$–$C_8$ polyhydroxyalkyl groups, $C_2$–$C_8$ aminoalkyl groups, mono($C_1$–$C_4$)alkylamino($C_1$–$C_4$)alkyl groups, di($C_1$–$C_4$)alkylamino($C_1$–$C_4$)alkyl groups and $C_1$–$C_8$ haloalkyl groups; wherein when at least one group chosen from $X_1$ and $X_2$ is a —$NR_1R_2$ group, then $R_1$ and $R_2$ of said —$NR_1R_2$ group may form, together with the nitrogen atom to which they are attached, a ring structure chosen from aromatic 4-, 5- and 6-membered rings and non-aromatic 4-, 5- and 6-membered rings;

$R_1$ and $R_2$, which may be identical or different, may also independently be chosen from aromatic 4-, 5- and 6-membered rings and non-aromatic 4-, 5- and 6-membered rings, wherein said rings may comprise at least one heteroatom;

A is a divalent group chosen from —CH=N— and —$CH_2$—NH—;

Z is a group chosen from a hydrogen atom, a halogen atom, aromatic 4-, 5- and 6-membered rings, non-aromatic 4-, 5- and 6-membered rings, $C_1$–$C_8$ alkyl groups, $C_1$–$C_8$ monohydroxyalkyl groups, $C_2$–$C_8$ polyhydroxyalkyl groups, $C_2$–$C_8$ aminoalkyl groups, mono ($C_1$–$C_4$)alkylamino($C_1$–$C_4$)alkyl groups, di($C_1$–$C_4$)alkylamino($C_1$–$C_4$)alkyl groups, $C_1$–$C_8$ haloalkyl groups, cyano groups and —$BR_3$ groups wherein B is a divalent group chosen from the groups:

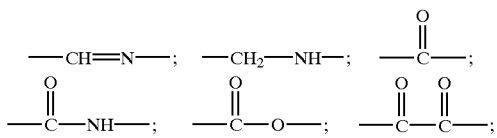

-continued

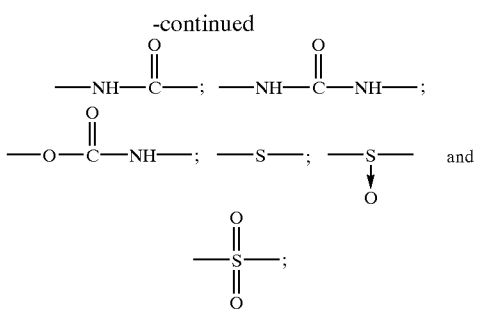

and wherein $R_3$ is chosen from $C_1$–$C_8$ alkyl groups, $C_1$–$C_8$ monohydroxyalkyl groups, $C_2$–$C_8$ polyhydroxyalkyl groups, $C_2$–$C_8$ aminoalkyl groups, mono ($C_1$–$C_4$)alkylamino($C_1$–$C_4$)alkyl groups, di($C_1$–$C_4$) alkylamino($C_1C_4$)alkyl groups and $C_1$–$C_8$ haloalkyl groups;

comprising directly coupling an aminoguanidine with a benzaldehyde derivative, wherein said benzaldehyde derivative may be substituted.

53. A process according to claim 52, wherein said direct coupling is carried out in an organic solvent.

54. A process according to claim 53, wherein said organic solvent is ethanol.

55. A process according to claim 53, wherein said direct coupling is carried out at a temperature ranging from 10° C. to the reflux temperature of said solvent.

56. A multi-compartment dyeing "kit", comprising a first compartment containing at least one dye composition comprising at least one compound of formula (I), or an acid addition salt thereof,

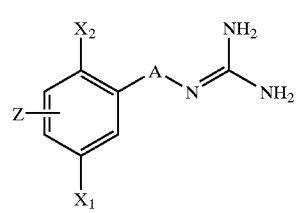

wherein:

$X_1$ and $X_2$, which may be identical or different, are each independently chosen from hydroxyl groups, —$NHR_1$ groups, and —$NR_1R_2$ groups, provided that $X_1$ and $X_2$ are not simultaneously a hydroxyl group;

$R_1$ and $R_2$, which may be identical or different, are each independently chosen from hydrogen atoms, $C_1$–$C_8$ alkyl groups, $C_1$–$C_8$ monohydroxyalkyl groups, $C_2$–$C_8$ polyhydroxyalkyl groups, $C_2$–$C_8$ aminoalkyl groups, mono($C_1$–$C_4$)alkylamino($C_1$–$C_4$)alkyl groups, di($C_1$–$C_4$)alkylamino($C_1$–$C_4$)alkyl groups and $C_1$–$C_8$ haloalkyl groups; wherein when at least one group chosen from $X_1$ and $X_2$ is a —$NR_1R_2$ group, then $R_1$ and $R_2$ of said —$NR_1R_2$ group may form, together with the nitrogen atom to which they are attached, a ring structure chosen from aromatic 4-, 5- and 6-membered rings and non-aromatic 4-, 5- and 6-membered rings;

$R_1$ and $R_2$, which may be identical or different, may also independently be chosen from aromatic 4-, 5- and 6-membered rings and non-aromatic 4-, 5- and 6-membered rings, wherein said rings may comprise at least one heteroatom;

A is a divalent group chosen from —CH=N— and —CH$_2$—NH—;

Z is a group chosen from a hydrogen atom, a halogen atom, aromatic 4-, 5- and 6-membered rings, non-aromatic 4-, 5- and 6-membered rings, C$_1$–C$_8$ alkyl groups, C$_1$–C$_8$ monohydroxyalkyl groups, C$_2$–C$_8$ polyhydroxyalkyl groups, C$_2$–C$_8$ aminoalkyl groups, mono(C$_1$–C$_4$)alkylamino(C$_1$–C$_4$)alkyl groups, di(C$_1$–C$_4$)alkylamino(C$_1$–C$_4$)alkyl groups, C$_1$–C$_8$ haloalkyl groups, cyano groups and —BR$_3$ groups wherein B is a divalent group chosen from the groups:

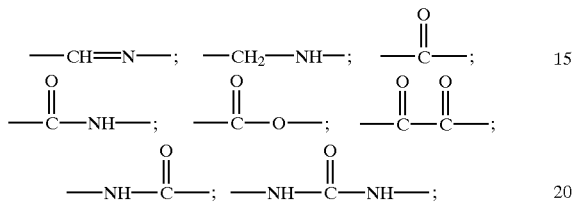

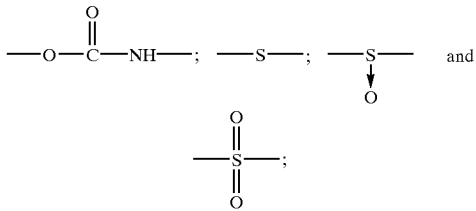

and wherein R$_3$ is chosen from C$_1$–C$_8$ alkyl groups, C$_1$–C$_8$ monohydroxyalkyl groups, C$_2$–C$_8$ polyhydroxyalkyl groups, C$_2$–C$_8$ aminoalkyl groups, mono(C$_1$–C$_4$)alkylamino(C$_1$–C$_4$)alkyl groups, di(C$_1$–C$_4$)alkylamino(C$_1$–C$_4$)alkyl groups and C$_1$–C$_8$ haloalkyl groups;

and a second compartment containing at least one oxidizing composition.

* * * * *

UNITED STATES PATENT AND TRADEMARK OFFICE
CERTIFICATE OF CORRECTION

PATENT NO. : 6,652,600 B2
DATED : November 25, 2003
INVENTOR(S) : Thierry Bordier et al.

It is certified that error appears in the above-identified patent and that said Letters Patent is hereby corrected as shown below:

Column 14,
Line 40, "2-phydroxyethyl" should read -- 2-ß-hydroxyethyl --.

Column 16,
Line 12, "Which" should read -- which --.

Column 17,
Line 63, "2-phydroxyethyl" should read -- 2- ß-hydroxyethyl --.

Column 18,
Line 1, "(ßhydroxyethyl)" should read -- (ß-hydroxyethyl) --.
Line 12, "(4aminophenyl)" should read -- (4-aminophenyl) --.
Line 22, "3hydroxymethylphenol" should read -- 3-hydroxymethylphenol --.

Column 19,
Line 2, "onedye" should read -- one dye --.

Signed and Sealed this

Twenty-third Day of March, 2004

JON W. DUDAS
*Acting Director of the United States Patent and Trademark Office*